(12) United States Patent  (10) Patent No.: US 8,571,813 B2
Johnston  (45) Date of Patent: Oct. 29, 2013

(54) FIBER OPTIC SENSOR SYSTEM FOR DETECTING SURFACE WEAR

(75) Inventor: Robert T. Johnston, Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 614 days.

(21) Appl. No.: 12/724,531

(22) Filed: Mar. 16, 2010

(65) Prior Publication Data

US 2011/0231110 A1 Sep. 22, 2011

(51) Int. Cl.
- *G01B 3/44* (2006.01)
- *G01N 3/06* (2006.01)
- G01N 3/56 (2006.01)
- G01M 11/08 (2006.01)
- G01M 5/00 (2006.01)

(52) U.S. Cl.
CPC *G01N 3/068* (2013.01); *G01N 3/56* (2013.01); *G01M 11/086* (2013.01); *G01M 5/0033* (2013.01)
USPC .......................................... 702/34

(58) Field of Classification Search
CPC ....... G01N 3/068; G01N 3/56; G01M 11/086; G01M 5/0033
USPC .......................................... 702/34
See application file for complete search history.

(56) References Cited

U.S. PATENT DOCUMENTS

| | | |
|---|---|---|
| 3,215,846 A | 11/1965 | McNaney |
| 3,315,160 A | 4/1967 | Goodman |
| 4,063,167 A | 12/1977 | Duly |
| 4,223,226 A * | 9/1980 | Quick et al. ............... 250/458.1 |
| 4,546,652 A | 10/1985 | Virkar et al. |
| 4,621,929 A * | 11/1986 | Phillips ........................... 374/43 |
| 4,655,077 A | 4/1987 | Purvis et al. |
| 4,733,068 A | 3/1988 | Thiele et al. |
| 4,743,787 A | 5/1988 | Bunner et al. |
| 4,758,065 A | 7/1988 | Dorman et al. |
| 4,884,434 A * | 12/1989 | Satake et al. ........................ 73/7 |
| 4,970,670 A | 11/1990 | Twerdochlib |
| 5,015,859 A * | 5/1991 | Uejio ........................ 250/358.1 |

(Continued)

FOREIGN PATENT DOCUMENTS

JP 57151803 A * 9/1982

OTHER PUBLICATIONS

Liu et al., Fluorescent Paint for Measurement of Heat Transfer in Shock-Turbulent Boundary Layer Interaction, Experimental Thermal and Fluid Science 1995; 10:101-112.*

(Continued)

*Primary Examiner* — Sujoy Kundu
*Assistant Examiner* — Timothy H Hwang

(57) ABSTRACT

One or more optical fibers (20, 20A, 20B, 20C, 20D), each with a second end (21) with a phosphor (26) disposed in a substrate (32) at a given depth ($D_n$) below a wear surface (34). A first photonic energy (52) is injected into a first end (19) of the optical fibers. The phosphor (26) emits a second photonic energy (54) into the fiber in response to the first photonic energy (52) incident on the phosphor from the fiber. When wear removes the phosphor (26) from one or more fibers, a detector (48, 49) detects a proportional reduction of the second photonic energy, indicating that wear has reached the given depth. A band-pass optical filter (46) may block wavelengths of the first photonic energy (52) from reflecting into the detector. The substrate temperature may be determined using a temperature-dependent emission of the phosphor.

18 Claims, 6 Drawing Sheets

(56) References Cited

U.S. PATENT DOCUMENTS

| | | | |
|---|---|---|---|
| 5,119,036 | A | 6/1992 | Rickards et al. |
| 5,440,300 | A | 8/1995 | Spillman, Jr. |
| 5,440,395 | A | 8/1995 | Makita |
| 5,760,593 | A | 6/1998 | Lawrence et al. |
| 5,797,414 | A | 8/1998 | Sirovich et al. |
| 5,867,302 | A | 2/1999 | Fleming |
| 5,905,260 | A * | 5/1999 | Sage et al. .................. 850/59 |
| 5,952,836 | A | 9/1999 | Haake |
| 5,969,260 | A | 10/1999 | Belk et al. |
| 5,970,393 | A | 10/1999 | Khorrami et al. |
| 6,034,296 | A | 3/2000 | Elvin et al. |
| 6,043,644 | A | 3/2000 | de Coulon et al. |
| 6,067,159 | A * | 5/2000 | Discenzo et al. ............ 356/450 |
| 6,080,982 | A | 6/2000 | Cohen |
| 6,109,783 | A | 8/2000 | Dobler et al. |
| 6,111,643 | A | 8/2000 | Discenzo et al. |
| 6,197,424 | B1 | 3/2001 | Morrison et al. |
| 6,262,550 | B1 | 7/2001 | Kliman et al. |
| 6,273,671 | B1 | 8/2001 | Ress, Jr. |
| 6,301,572 | B1 | 10/2001 | Harrison |
| 6,331,823 | B1 | 12/2001 | El-Ibiary |
| 6,343,251 | B1 | 1/2002 | Herron et al. |
| 6,366,201 | B1 | 4/2002 | Hanisko |
| 6,512,379 | B2 | 1/2003 | Harrold et al. |
| 6,516,671 | B2 | 2/2003 | Romo et al. |
| 6,523,383 | B2 | 2/2003 | Joki et al. |
| 6,532,412 | B2 | 3/2003 | Adibhatla et al. |
| 6,556,956 | B1 | 4/2003 | Hunt |
| 6,576,861 | B2 | 6/2003 | Sampath et al. |
| 6,591,182 | B1 | 7/2003 | Cece et al. |
| 6,667,725 | B1 | 12/2003 | Simons et al. |
| 6,670,046 | B1 | 12/2003 | Xia |
| 6,687,436 | B2 | 2/2004 | Griffin |
| 6,717,420 | B2 | 4/2004 | Eyraud et al. |
| 6,723,379 | B2 | 4/2004 | Stark |
| 6,735,549 | B2 | 5/2004 | Ridolfo |
| 6,756,908 | B2 | 6/2004 | Gass et al. |
| 6,760,689 | B2 | 7/2004 | Folin et al. |
| 6,796,187 | B2 | 9/2004 | Srinivasan et al. |
| 6,816,817 | B1 | 11/2004 | Retlich et al. |
| 6,822,440 | B2 | 11/2004 | Machul |
| 6,831,555 | B1 | 12/2004 | Miller et al. |
| 6,838,157 | B2 | 1/2005 | Subramanian |
| 6,868,711 | B2 * | 3/2005 | Ebi ........................ 73/7 |
| 7,038,201 | B2 * | 5/2006 | Nichols .................... 250/302 |
| 7,154,081 | B1 * | 12/2006 | Friedersdorf et al. ... 250/227.14 |
| 7,270,890 | B2 * | 9/2007 | Sabol et al. ................ 428/632 |
| 7,368,827 | B2 | 5/2008 | Kulkarni et al. |
| 7,432,821 | B1 | 10/2008 | Mastro et al. |
| 7,551,268 | B2 | 6/2009 | Discenzo |
| 7,551,288 | B1 | 6/2009 | Discenzo |
| 2002/0170890 | A1 | 11/2002 | Keicher et al. |
| 2006/0056959 | A1 * | 3/2006 | Sabol et al. ................ 415/118 |
| 2007/0163325 | A1 | 7/2007 | Radzisewski et al. |

OTHER PUBLICATIONS

Eduardo Castillo-Castaneda; On-line Wear Detection of Milling Tools Using a Displacement Fiber Optic Sensor; Journal of Applied Research and Technology, Jul. 2003, pp. 164-174, ISSN 1665-6423, Mexico.

* cited by examiner

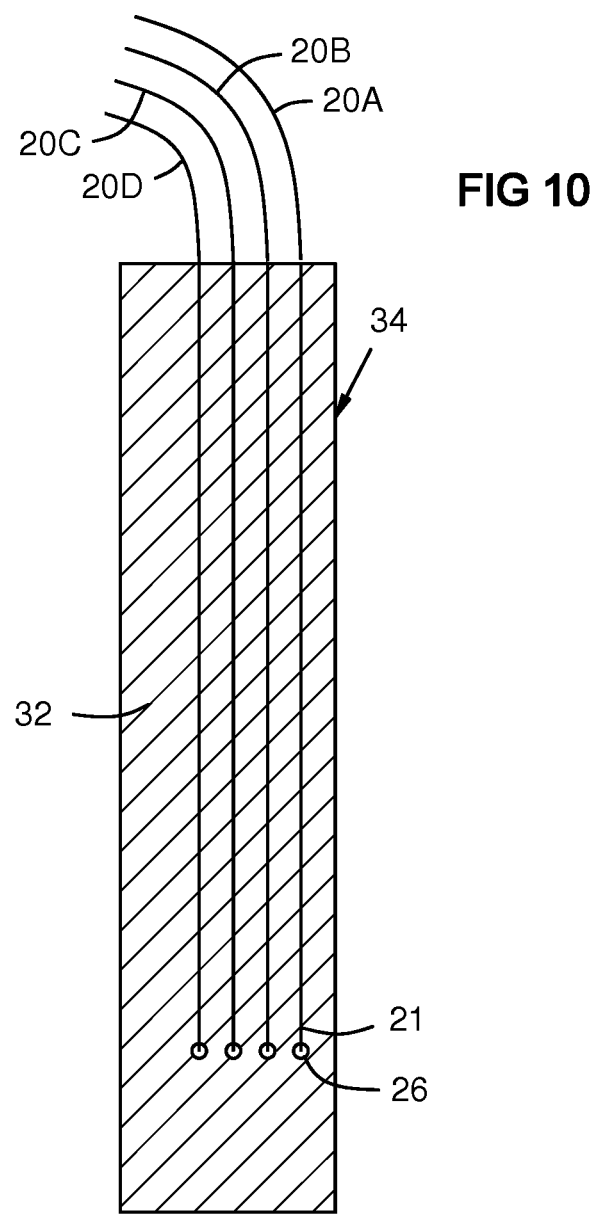

FIBER OPTIC SENSOR SYSTEM FOR DETECTING SURFACE WEAR

FIELD OF THE INVENTION

The invention relates to sensors imbedded in a surface for detecting wear that reduces the surface, and to sensor systems that quantify such wear.

BACKGROUND OF THE INVENTION

Surface-reducing wear occurs in machines by frictional contact of adjacent parts and by other forms of erosion. For example, turbine engines have bearings, shroud liners, combustor liner spring clips, and other areas where reduction wear occurs. Detecting such wear can be critical to safe operation of the machine.

Sensors have been designed to detect wear without disassembly of components. For example, electrical conductors may be embedded in a wear surface. A detector connected to these conductors senses an open circuit caused by wear through a conductor, and determines a wear depth. An example is U.S. Pat. No. 7,270,890.

U.S. Pat. No. 4,884,434 describes loops of optical fibers embedded in a wear surface. Each loop forms an optical circuit with a light source at one end and a detector at the other end. Reduction wear breaks one or more loops in succession, which is detected by respective losses of signal. This design requires enough sensor area for the embedded fibers to form loops, and requires both a source leg and a detector leg of each fiber loop to pass through the sensor block to the source and detector.

U.S. Pat. No. 5,440,395 describes a conical depression in the backside of a shroud liner on the inner surface of a turbine casing. As the shroud is abraded by the rotating turbine blades, the conical depression forms a progressively larger hole in the liner. Light is reflected backward off the conical depression into a detector. Reduction in the reflected light is interpreted via a formula as respective wear depth. However, this device requires a hole in the shroud liner. Entry of combustion gas and particles must be blocked by purge air, which is not needed in the present invention.

U.S. Pat. No. 6,111,643 describes an optical fiber in a wear surface. Light injected into the fiber reflects off the opposed abrading surface and returns through the same fiber. The fiber tip wears along with the wear surface, and the light circuit length is reduced. This length is measured by interferometry to determine a wear depth. The present invention does not analyze reflection from the abrading surface, which requires signal analysis that deals with variable reflectivity, and the present invention does not require interferometry, thus eliminating elements such as reference beam optics.

BRIEF DESCRIPTION OF THE DRAWINGS

The invention is explained in the following description in view of the drawings that show:

FIG. 10 shows an embodiment with fibers parallel to the wear surface.

DETAILED DESCRIPTION OF THE INVENTION

Figure 1:
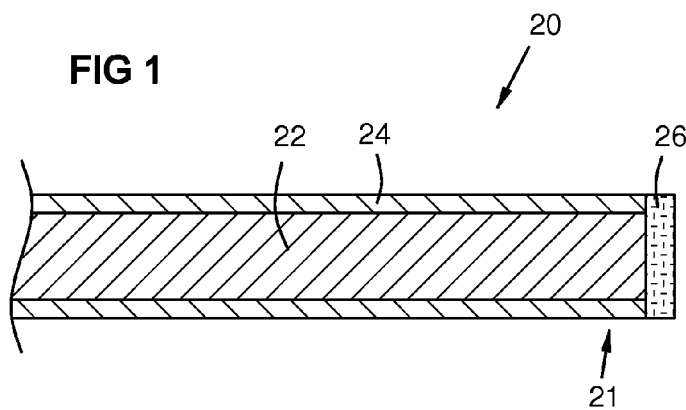
FIG. 1 is a sectional view of a sensor end of an optical fiber per aspects of the invention.

The present invention uses one or more optical fibers 20. Each fiber has a sensor end 21 disposed in a substrate 32 at a given depth below a wear surface 34. The sensor end has a re-emission material 26 that emits a second photonic energy into the fiber in response to a first photonic energy received from the fiber. When erosion of the surface 34 erodes the re-emission material 26, the resulting reduction of the second photonic energy indicates that wear has reached the given depth.

FIG. 1 is a sectional view of an optical fiber 20, which may have a core 22 and cladding 24 as known in the art. The optical fiber 20 may be made of optical glass, plastic, or other materials per technology known in the art. For high-temperature applications, silica-based optical fiber waveguides are known to provide operating temperatures up to about (900° C./1650° F.). Sapphire-based optical waveguides are known to provide operating temperatures up to about (2000° C./3600° F.).

According to aspects of the invention, the optical fiber 20 has a sensor end 21 with a re-emission material 26. Herein "re-emission" means the re-emission of energy from incident photons by fluorescence, phosphorescence, or reflection. The re-emission may have a different wavelength than the incident energy. As an example, Cerium-doped yttrium aluminum garnet ($Y_3Al_5O_{12}$:Ce or YAG:Ce) is known as a light-converting phosphor in light-emitting diodes (LEDs). It emits yellow light when excited by blue, ultraviolet, or x-ray light, and has a melting point of 1950° C. In contrast, a reflective material may reflect some or all of the incident wavelengths, but at a higher efficiency than any reflection that may occur from the opposed abrading surface after removal of the fiber end. Dielectric mirrors can have efficiencies of over 99% in a narrow band, so reflected energy from such mirror can be distinguished from reflections of the opposed abrading surface. Herein "re-emitter" means a material, combination of materials, or device that re-emits incident photonic energy.

Figure 2:
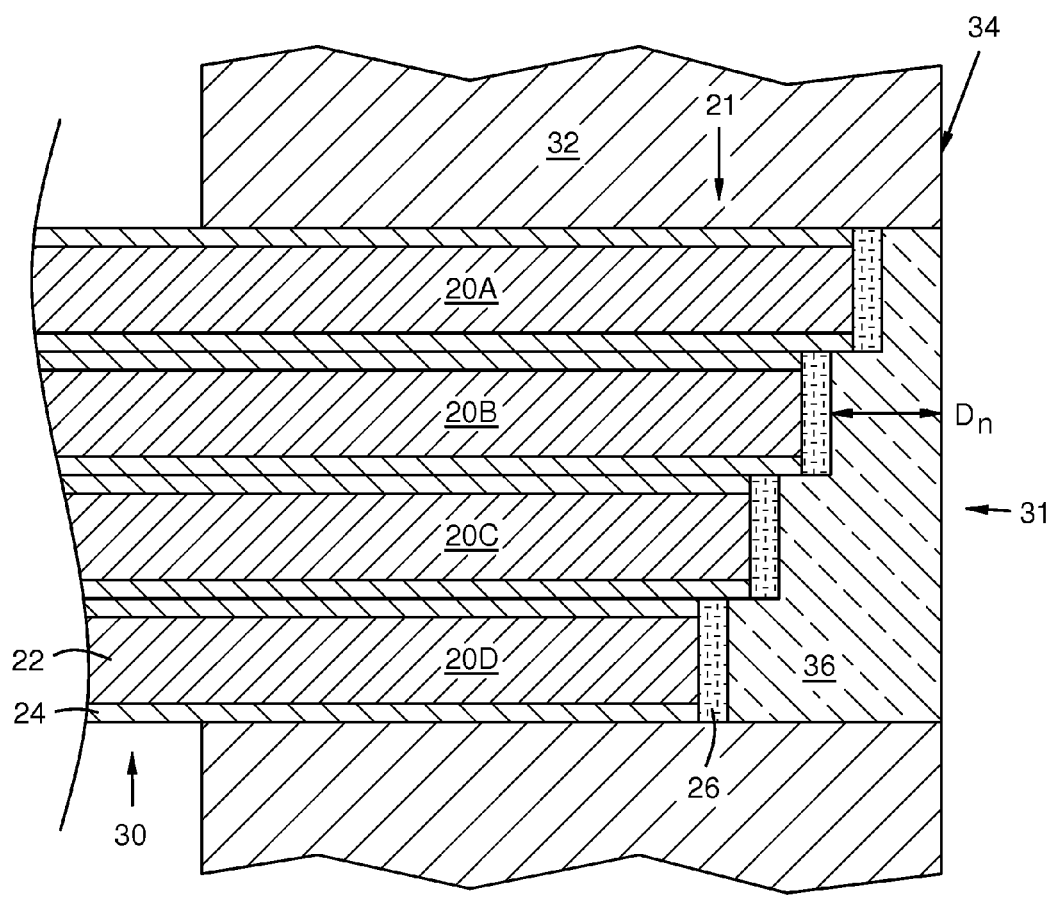
FIG. 2 is a sectional view of a plurality of optical fibers in a substrate with sensor ends at different depths below a wear surface per aspects of the invention.

FIG. 2 shows a bundle 30 of optical fibers 20A, 20B, 20C, 20D with re-emission material 26 on ends disposed at respective different given depths $D_n$ below a wear surface 34 in a substrate 32. A filler material 36 may provide a flush surface. The fiber bundle 30 may be impregnated in a block of filler material 36 to form a sensor plug 31, which may be threaded, not shown. Each fiber 20A, 20B, 20C, and 20D may optionally represent a tow of multiple fibers for each given depth. The re-emission material 26 may be individually applied to each fiber or tow. Alternatively, to simplify manufacturing, it can be applied to the whole sensor end 21 at once.

Figure 3:
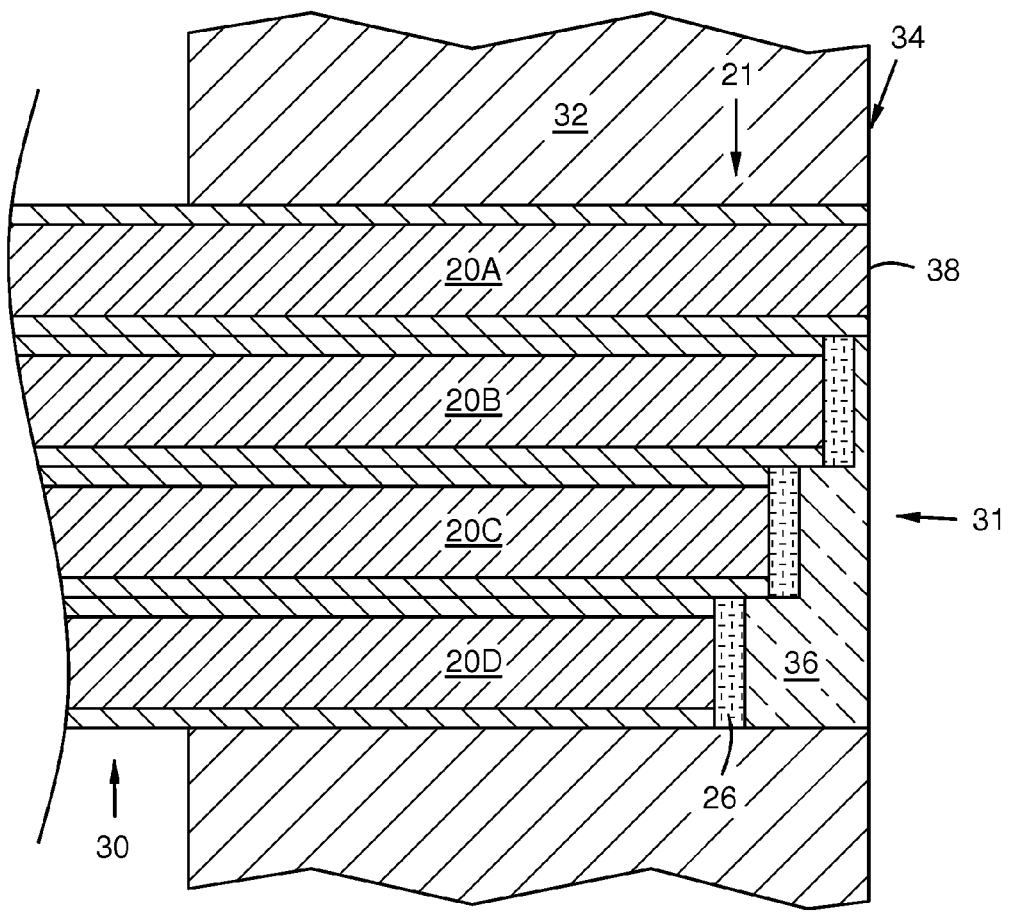
FIG. 3 is a view as in FIG. 2 after surface wear has removed the sensor end of a first optical fiber.

FIG. 3 shows a view of FIG. 2 after wear has occurred to a depth that removes the re-emission material 26 from the end 38 of the shallowest sensor fiber or tow 20A. This reduces the photonic re-emission return signal of fiber or tow 20A to zero, and reduces the total return signal of the fiber bundle by a detectable step.

Figure 4:
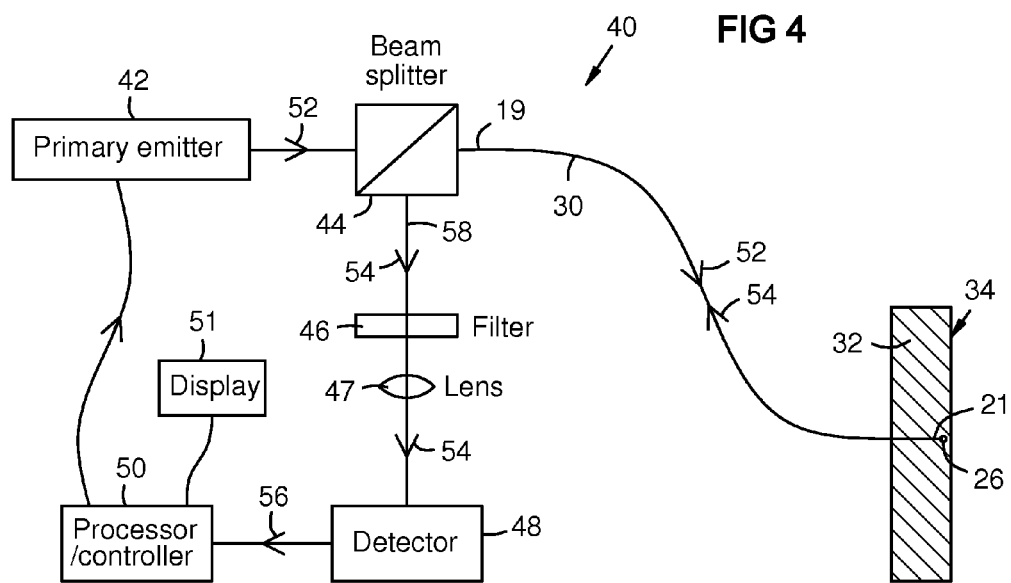
FIG. 4 is a schematic view of a wear depth monitoring system per aspects of the invention.

FIG. 4 is a schematic view of a sensor system 40, with a primary emitter 42 such as a laser, a coupler or beam splitter 44, a fiber optic bundle 30 formed of one or more optical fibers with respective sensor ends 21, an optical filter 46, a focusing lens 47, and a photo-detector 48 such a Charge Coupled Device (CCD) array. The detector 48 may provide analog or digital electronic signals 56 to a processor/controller 50 for analysis, maintenance scheduling, and/or display 51.

The primary emitter 42 injects a first photonic energy 52 into a first end 19 of the fibers 30, which travels to the sensor ends 21. In response, the re-emission material 26 on each fiber emits second photonic energy 54 back into the fibers. A portion of the second energy is diverted by the splitter 44 into a detection route or line 58. An optical band-pass filter may admit only a characteristic band of the second photonic energy for detection. This eliminates reflections of the first photonic wavelength that may otherwise overwhelm the re-emission signal.

Figure 5:
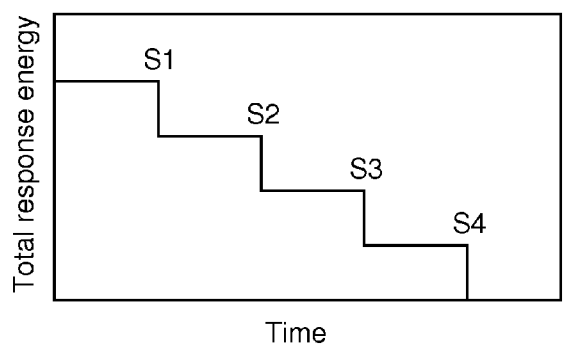
FIG. 5 shows a total return amplitude curve for the sensor of FIGS. 2 and 3, where each step indicates that a given sensor end has been eroded.

FIG. 5 illustrates a stepwise response function over time provided by the sensors of FIGS. 2 and 3, when the re-emission of all fibers 20A-20D is detected as a total return. Each step S1, S2, S3, and S4, indicates that wear has reached a given depth $D_n$.

Figure 6:
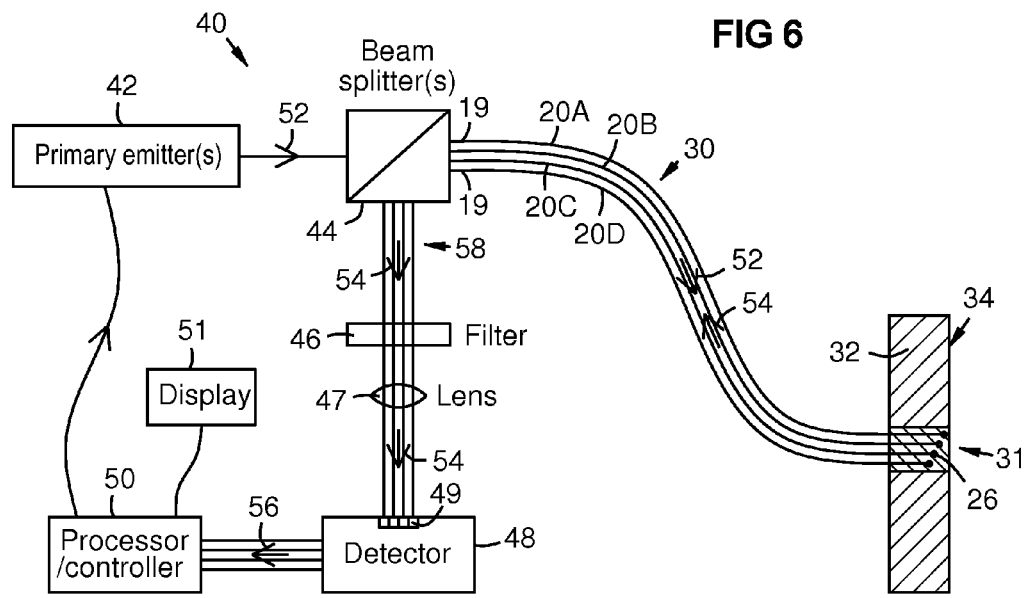
FIG. 6 illustrates a system embodiment in which a fiber or tow for each depth is individually detected and analyzed.
Figure 7:
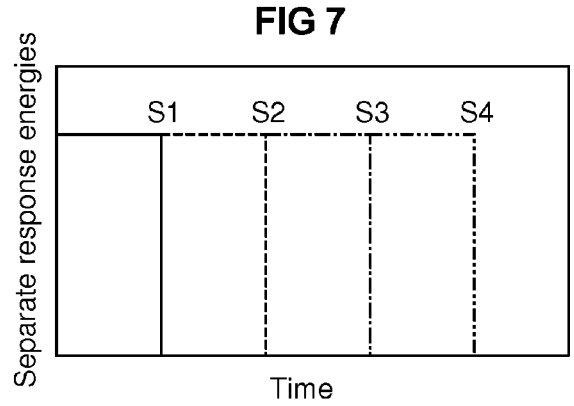
FIG. 7 shows an individual return amplitude function for each fiber or tow individually detected in FIG. 6.

FIG. 6 illustrates a sensor system in which each fiber or tow 20A, 20B, 20C, 20D is detected individually, for example by individual elements of a CCD array 49 in the detector 48. The plurality of electronic signals 56 shown in FIG. 6 is schematic only. A single physical communication line 56 may provide information for each individual fiber or tow, for example by an electronic signal representing a time series of linear arrays of binary integers. The response for each fiber or tow 20A, 20B, 20C, 20D drops to zero when the respective re-emission material is removed, as shown in FIG. 7.

Figure 8:
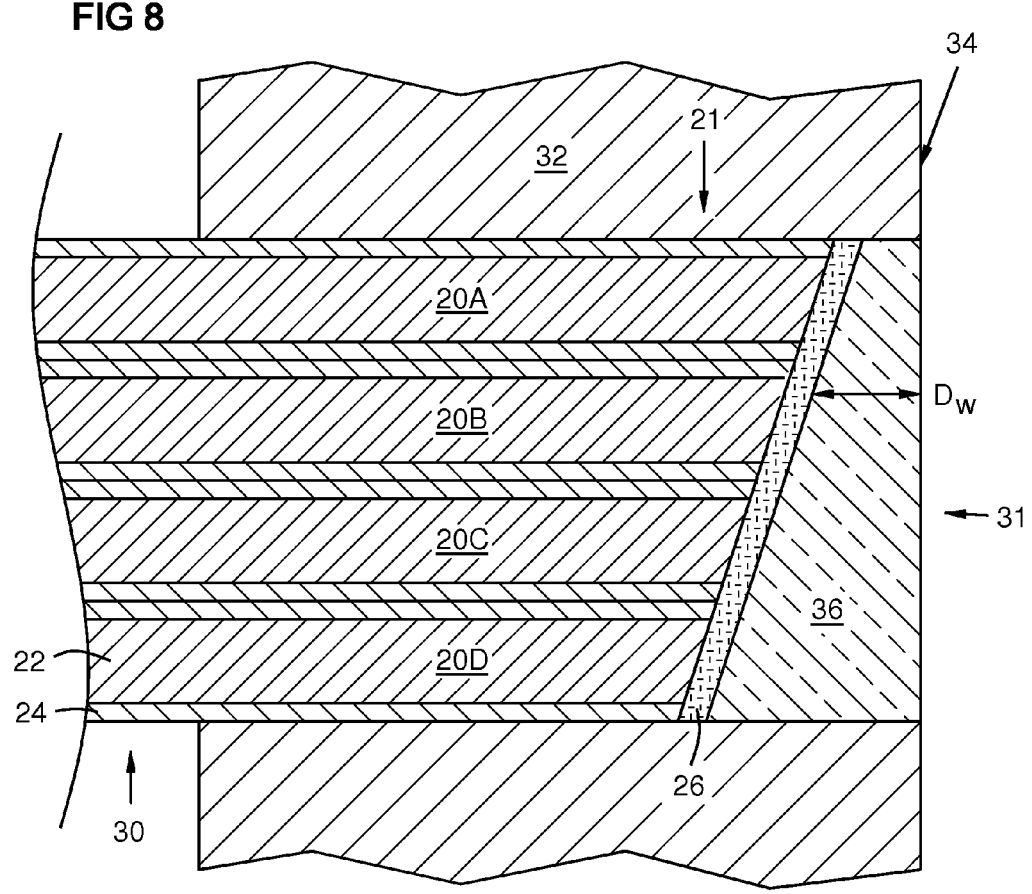
FIG. 8 is a sectional view of a sensor end with a continuously varying depth.
Figure 9:
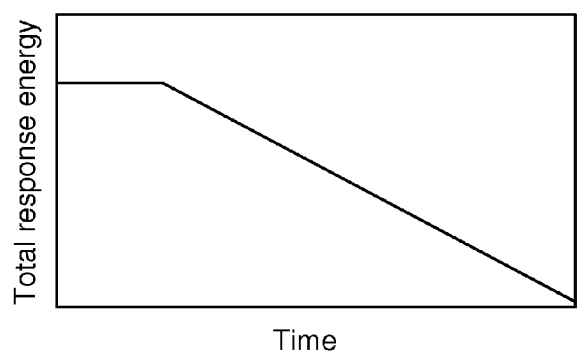
FIG. 9 shows a total return amplitude function for the sensor of FIG. 8.

FIG. 8 is a sectional view of a sensor end 21 as in FIG. 2, but having a continuously varying depth D. FIG. 9 shows a total response function for the sensor of FIG. 8. An individual return amplitude function for this sensor embodiment is also possible, using the configuration of FIGS. 6 and 7. Advantages of this sensor embodiment include: 1) Continuously response function provides continuous wear progress; and 2) Manufacturing may be simplified, since the end of a flat fiber cable can be simply sliced at an angle and coated with a phosphor using known processes. The ends 21 are shown aligned for clarity, but they may alternately follow a curve, as by curling a flat cable around a mandrel oriented with the cable. Thus, the sensor ends 21 may be oriented substantially normally to the wear surface 34 and may be adjacent to each other in a line or curve that is not parallel to the wear surface 34.

FIG. 10 shows an embodiment with fibers 20A, 20B, 20C, 20D that are parallel to the wear surface 34. This geometry covers a larger wear area than fibers normal to the wear surface as previously shown. It detects the worst-case area of wear, since a break anywhere along a fiber produces the same result—the return amplitude of the fiber drops to zero.

A re-emission material 26 may be chosen that has a temperature-dependent characteristic such as the shape of the response curve and/or the wavelength. For example, Dysprosium-doped $Y_3Al_5O_{12}$ (Dy:YAG) is a known temperature-sensitive phosphor that can be excited by a laser pulse, and produces temperature-dependent fluorescence. It is sensitive in ranges of 30-1430° C. Samarium-doped $Y_3Al_5O_{12}$ (Sm:YAG) is another known temperature-sensitive phosphor similar to Dy:YAG. Such phosphors allow thermometry to be performed by means such as optical pulse signal/response analysis and/or spectroscopy, for example, as described in U.S. Pat. No. 4,223,226, which is incorporated herein by reference.

Fluorescent paint could be used as an alternative to phosphor coatings at lower operating temperatures. Fluorescent paint reacts to long-wave ultraviolet (UV) radiation. The emission is usually in the visible wavelengths. A narrow band pass optical filter may be used to separate the emitted light from the illuminating light, thereby allowing the wear depth and the temperature to be measured, similar to the phosphor example above.

To incorporate thermometry herein, elements from U.S. Pat. No. 4,223,226 FIG. 2 or 5 may be added to the present systems of FIG. 4 or 6. To incorporate the pulsed signal/response embodiment of U.S. Pat. No. 4,223,226, the present processor/controller 50 of FIG. 4 may activate, and analyze responses to, a series of optical pulses such as shown in FIGS. 3-3e of U.S. Pat. No. 4,223,226. In addition, the present processor/controller 50 may recognize reductions in successive amplitudes of responses to the pulses as being due to wear. Thus, it can determine both the temperature and the wear depth from the same simple sensor embodiments shown and described herein by using a temperature-dependent phosphor. The primary emitter 42 herein may be pulsed under control of the processor/controller 50.

Alternately, the present processor of FIG. 6 may analyze each fiber or tow individually, in which case the response from a given fiber or tow to the pulse sequences (FIGS. 3a-3e of U.S. Pat. No. 4,223,226) drops to zero when the sensor end of the respective fiber or tow is worn away.

To incorporate the spectroscopy embodiment of U.S. Pat. No. 4,223,226 FIG. 5, the prism 46 thereof may be added to the present system of FIG. 4 or 6 between the present lens 47 and detector 48. The present detector 48 may incorporate a wavelength detection device as described for FIG. 5 of U.S. Pat. No. 4,223,226 for either the total signal (per FIG. 4 herein) or for each individual signal (per FIG. 6 herein). The present processor/controller 50 may convert the wavelength information to temperature data as described in U.S. Pat. No. 4,223,226. In addition, the present processor/controller 50 may recognize reductions in amplitudes of responses as being due to wear. Thus, it can determine both the temperature and the wear depth from the same simple sensor embodiments described herein by using a temperature-dependent phosphor.

Combining thermometry and wear detection in this way is especially cost-effective. Only a single optical fiber in one direction is needed for each depth to be measured, as opposed to a fiber loop for each depth as in U.S. Pat. No. 4,884,434. This allows the present sensor plug 31 to be small and inexpensive. In contrast to U.S. Pat. No. 6,111,643, the present sensor end 21, 26 is self-contained. It does not require reflections from an opposed machine surface that can be unpredictable, and can change with time and supplier. Interferometry is not needed in the present invention for depth analysis, because simple reductions in the response energy indicate the depth.

Embodiments of the present invention may also be used to determine the heat transfer rate through a substrate 32 by determining the temperature at specific depths within the substrate and applying the equation:

$$Q = (\text{delta } T)/R \qquad \text{(Equation 1)}$$

where Q is the heat transferred, delta T is the change in temperature over distance into the substrate, and R is the thermal resistance of the material over that distance. This calculation may be performed by the same processor used to determine a depth of wear. The fibers in such an embodiment may be kept as small as possible to improve the accuracy of the information, and they may be individual fibers rather than a bundle to gather the temperature data at farther distances apart.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A sensor system that detects reduction wear in a surface, comprising:
a first optical fiber comprising first and second ends;
the second end of the first optical fiber disposed at a first depth in a substrate beneath a wear surface;
a primary emitter that injects a first photonic energy into the first end of the optical fiber;
a re-emitter on the second end of the optical fiber that emits a second photonic energy into the second end of the first optical fiber in response to the first photonic energy being incident on the re-emitter via the optical fiber;
a detector that detects the second photonic energy emergent from the first end of the first optical fiber; and
a processor connected to the detector that calculates a wear depth in the wear surface according to a characteristic of the second photonic energy;
wherein the second photonic energy comprises a different wavelength than the first photonic energy, and further comprising a band-pass filter that blocks wavelengths of the first photonic energy emergent from the first end of the optical fiber before reaching the detector.

2. The sensor system of claim 1, further comprising:
a second optical fiber comprising first and second ends;
the second end of the second optical fiber being adjacent to the first optical fiber and disposed at a second depth in the substrate different than the first depth beneath the wear surface;
a re-emitter disposed on the second end of the second optical fiber to emit second photonic energy into the second end of the second optical fiber in response to first photonic energy being incident on the re-emitter via the second optical fiber.

3. The sensor system of claim 2, wherein the detector detects a total amplitude of second photonic energy emergent from the first ends of the first and second optical fibers, and the processor interprets progressive reductions in the total return amplitude as progressive wear to the first and second depths.

4. The sensor system of claim 2, wherein the detector detects a return amplitude of second photonic energy emergent from the first and second optical fibers individually, and the processor interprets a drop to zero in the return amplitude from the first and second optical fibers individually as progressive wear reaching the depth of the second end of the first and second optical fibers respectively.

5. The sensor system of claim 2, wherein the re-emitter comprises a material that produces a temperature-dependent characteristic in the second photonic energy, and the detector detects the temperature-dependent characteristic, and the processor interprets the temperature-dependent characteristic to produce both a temperature and a wear depth indication.

6. A sensor system that detects reduction wear in a surface, comprising:
a plurality of optical fibers, each comprising first and second ends, the second ends of the optical fibers proximate each other at a respective plurality of depths in a substrate beneath a wear surface;
a source of a first photonic energy directed into the first ends of the optical fibers;
a re-emitter proximate the second ends of the optical fibers that emits a second photonic energy into said second ends in response to the first photonic energy incident on the re-emitter via the optical fibers;
a detector that detects the second photonic energy emergent from the first ends of the first optical fibers; and
a processor connected to the detector that calculates a wear depth in the wear surface according to a characteristic of the second photonic energy;
wherein the second photonic energy comprises a different wavelength than the first photonic energy, the system further comprising an optical band-pass filter that blocks wavelengths of the first photonic energy emergent from the first end of the optical fiber before reaching the detector.

7. The sensor system of claim 6, wherein the detector detects a total amplitude of the second photonic energy emergent from the first ends of the plurality of optical fibers, and the processor interprets progressive reductions in the total return amplitude as progressive wear to the respective plurality of depths.

8. The sensor system of claim 6, wherein the detector detects a return amplitude of the second photonic energy emergent from the first end of each of the plurality of fibers individually, and the processor interprets a drop to zero in the return amplitude of each optical fiber as wear reaching the respective depth of the second end of each optical fiber.

9. The sensor system of claim 6, wherein the re-emitter comprises a material that produces a temperature-dependent characteristic in the second photonic energy, and the detector detects the temperature-dependent characteristic, and the processor interprets the temperature-dependent characteristic in the second photonic energy to produce both a temperature indication and a wear depth indication.

10. The sensor system of claim 6, wherein a total amplitude of the second photonic energy from the plurality of optical fibers is proportional to a number of the plurality of optical fibers remaining undamaged by a progression of wear in the wear surface; wherein the detector communicates a signal representing the total amplitude to the processor, and the processor calculates the wear depth based on the total amplitude representing the proportion of the plurality of optical fibers remaining undamaged.

11. The sensor system of claim 6, wherein the plurality of optical fibers comprise portions extending from the second ends thereof that are oriented substantially normally to the wear surface.

12. The sensor system of claim 6, wherein the plurality of optical fibers comprise portions extending from the second ends thereof that are in the substrate and are oriented substantially parallel to the wear surface.

13. The sensor system of claim 6, wherein the re-emitter comprises a re-emission material on the second end of each of the plurality of optical fibers.

14. The sensor system of claim 6, wherein the re-emitter comprises a re-emission material covering the second ends of the plurality of fibers as a group.

15. The sensor system of claim 14, wherein second ends of the optical fibers are oriented substantially normally to the wear surface, and are adjacent to each other along a line or curve that is non-parallel to the wear surface.

16. The sensor system of claim 6, wherein the re-emitter comprises a material that produces a temperature-dependent characteristic in the second photonic energy, and the detector detects the temperature-dependent characteristic, and the processor interprets the temperature-dependent characteristic in the second photonic energy to produce both a temperature indication and a heat transfer indication.

17. A sensor system that detects reduction wear in a surface, comprising:
- a plurality of optical fibers, each comprising first and second ends, the second ends of the optical fibers adjacent to each other at a respective plurality of depths in a substrate beneath a wear surface;
- a source of a first photonic energy directed into the first ends of the optical fibers;
- a re-emission material on the second end of each of the optical fibers that emits a second photonic energy into said second ends in response to the first photonic energy incident on the re-emission material via the optical fibers;
- a detector that detects the second photonic energy emergent from the first ends of the first optical fibers; and
- a processor connected to the detector that calculates a wear depth in the wear surface according to a characteristic of the second photonic energy;
- wherein the second photonic energy comprises a different wavelength than the first photonic energy, the system further comprising an optical band-pass filter that blocks wavelengths of the first photonic energy emergent from the first end of the optical fiber before reaching the detector.

18. The sensor system of claim 17, wherein second ends of the optical fibers are oriented substantially normally to the wear surface, and are adjacent to each other along a line or curve that is non-parallel to the wear surface.

\* \* \* \* \*